(12) United States Patent
Edelson et al.

(10) Patent No.: US 6,690,386 B2
(45) Date of Patent: Feb. 10, 2004

(54) MEDICAL IMAGE DISPLAY SYSTEM

(75) Inventors: Steven D. Edelson, Wayland, MA (US); Klaus Diepold, Siegertsbrunn (DE)

(73) Assignee: DynaPel Systems, Inc., New York, NY (US)

( * ) Notice: Subject to any disclaimer, the term of this patent is extended or adjusted under 35 U.S.C. 154(b) by 279 days.

(21) Appl. No.: 09/867,676

(22) Filed: May 31, 2001

(65) Prior Publication Data

US 2002/0180761 A1 Dec. 5, 2002

(51) Int. Cl.[7] .............................. G09G 5/02; G09G 5/00; G06K 9/00; A61B 8/04
(52) U.S. Cl. ..................... 345/634; 345/606; 345/643; 382/131; 600/443
(58) Field of Search ................................ 345/418, 424, 345/427, 586, 606, 630, 634, 632, 633, 638, 643; 382/128, 130, 131, 132; 378/20, 21, 29, 30, 45, 87–89, 98; 600/424, 425, 443, 444, 449, 160; 705/2; 348/45

(56) References Cited

U.S. PATENT DOCUMENTS

| | | | | |
|---|---|---|---|---|
| 5,766,129 A | * | 6/1998 | Mochizuki | 600/443 |
| 5,910,111 A | * | 6/1999 | Hunziker | 600/407 |
| 6,083,168 A | * | 7/2000 | Hossack et al. | 600/443 |
| 6,162,174 A | * | 12/2000 | Friemel | 600/447 |
| 6,201,900 B1 | | 3/2001 | Hossack | |
| 6,252,399 B1 | * | 6/2001 | Pruessmann et al. | 324/307 |
| 6,351,545 B1 | * | 2/2002 | Edelson et al. | 382/107 |

\* cited by examiner

Primary Examiner—Matthew C. Bella
Assistant Examiner—Wesner Sajous
(74) Attorney, Agent, or Firm—Venable, LLP; Ralph P. Albrecht

(57) ABSTRACT

In a system for displaying medical images, medical images are generated from views internally within a body by means of x-rays, CAT scan, or MRI. The images are spaced in time or are views of spaced slices through tissue or through an organ within a body. The spacing between the images is such that the display of the images as a motion picture would result in the motion being depicted as jerky in the motion picture. A video processor generates dense motion vector fields between adjacent frames of the original set of images and, from the dense motion vector fields, generates interpolated images between the images of the original set. The interpolated images are assembled into a motion picture set of images, which are displayed by a video display device.

18 Claims, 2 Drawing Sheets

MEDICAL IMAGE DISPLAY SYSTEM

This invention relates to a system for improving the display of medical images of internal organs and tissue such as produced by x-ray, CAT scan, or MRI.

BACKGROUND OF THE INVENTION

Medical images of internal organs and tissue are typically viewed one frame at a time. This process is time consuming and it may result in significant diagnostic indicia being overlooked wherein the diagnostic indicia is represented by changes or differences between related medical images such as images taken at successive time intervals or images which are taken from spatially separated slices through internal organs or tissue. Accordingly, there is a need to display medical images in a manner to make such changes or differences more noticeable. One way to make changes more noticeable is to display successive images as a motion picture. In the case of successive images displaced in time, the images would appear as a motion picture provided the successive images are taken at short enough intervals to avoid excessive changes from image to image. In a practical system, the display of such successive images does not result in a motion depiction in which the depicted objects transform smoothly, because the changes between the successive images are too great and abrupt changes typically occur from image to image resulting in the depiction being "jerky" and difficult to follow. The above problem, of course, could be solved by simply taking the images closer together in time. But this solution is impractical, if not impossible, because of the number of images required and the time required to obtain each image.

SUMMARY OF THE INVENTION

In accordance with invention, a series of related medical images are generated by x-ray, CAT scan, or MRI. The images may be taken at regular or irregular time intervals or they may be taken from regular or irregular spaced slices through an organ or tissue.

In the case of successive images corresponding to incrementally spaced slices through an organ or tissue, the successive images can be shown as a motion picture. In such a display, the depicted organs or tissue will appear to transform their shape and characteristics as the successive images are displayed. If the slices are close enough together, the resulting display will appear as a quality motion picture, in which the depicted organs or tissue transform smoothly as the successive images are displayed.

In the preferred embodiment, the images are spaced temporally or spatially in accordance with what is practical, resulting in substantial changes between successive images, so that a display of the successive images as a motion picture would not provide a smooth depiction of the transformation of the depicted image objects. The medical images, if not already represented as pixels in digital form, are converted to such form. The resulting image data is then analyzed to generate dense motion vector fields representing the apparent motion of image elements from the frame to frame in the sequence of related medical image frames. When the successive images are at successive intervals of time the image elements represent small pixel sized pieces of depicted objects. If an object is moving or changing as represented in adjacent frames, then the image elements of such objects will move with the object. If a depicted the object is stationary then the dense motion field vectors will be zero for the image element making up the stationary object. A dense motion field comprising a vector for each pixel, will be generated for each pair of adjacent frames.

When the sequence of medical images represents spaced slices through an organ or tissue, the same image elements will usually not be found in successive frames, since each frame will represent a different slice. The dense motion vector field analysis will never-the-less locate corresponding image elements in successive frames as if the successive frames represented motion from frame to frame, and the vectors of the dense motion vector field will represent any displacement between the corresponding image elements in successive frames.

In accordance with the invention, the dense motion vector fields are used to generate interpolated frames between the original sequence of frames. The interpolated frames are interlaced with the original sequence of frames so that when the sequence of frames with the interpolated frames are displayed in sequence at a motion picture rate, i.e. at least 15 frames per second, the change between successive frames will be depicted as smooth motion or transformation from frame to frame.

DESCRIPTION OF A PREFERRED EMBODIMENT

Figure 1:
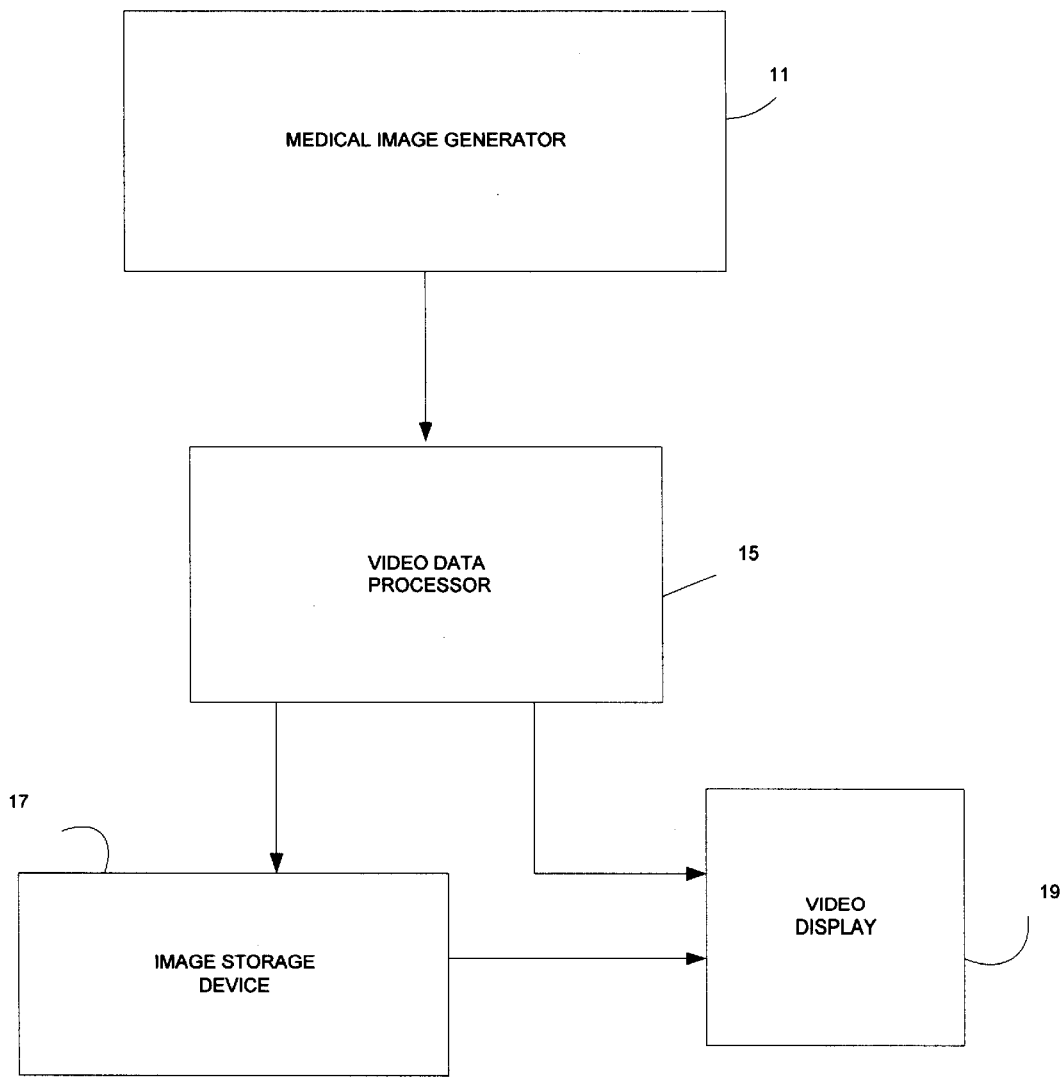
FIG. 1 is a block diagram illustrating the system of the invention.
Figure 2:
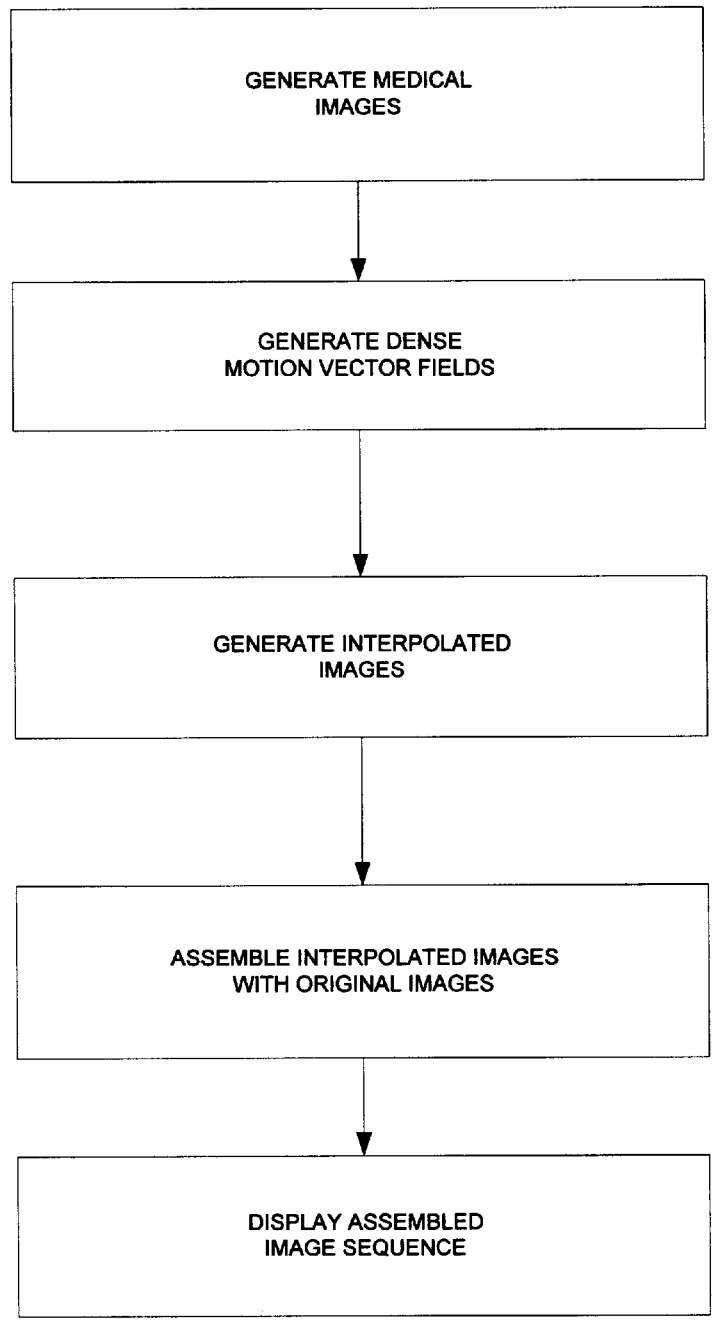
FIG. 2 is a flowchart illustrating the process of the invention.

As shown in FIG. 1 the system of the invention comprises a medical image generator 11. The medical image generator may be an x-ray camera, a CAT scan imager, or an MRI, designed to obtain images internally within the human body or in the body of an animal, such as images of organs or tissue. The images may be successive images spaced in time of the same component or part of a body, or in the case as CAT scan images or MRI images the images may be of spaced slices through one or more organs or tissue.

The images obtained by the image generator 11 converted to pixel data if necessary. In the case of many medical image sources, such as MRI, the images will already be in digital form. If the medical images are in the form of analog video images, they are converted to pixel data by a video decoder. The frames of pixel data are applied to a video data processor 15, which analyzes the pixel data and determines dense motion vector fields between each adjacent pair of frames in the sequence of images. As indicated above, if the pixel data frames represent successive images in time, the dense motion vector field will represent the displacement of image elements from frame to frame wherein each image element is a pixel sized piece of a depicted object which may have moved from one frame to the next. If a depicted object is stationary, then the motion vectors for the image elements of such stationary object will be zero. It should be noted that image elements are similar to pixels but are not the same thing as pixels. Pixels are stationary from frame to frame, whereas image elements will move with any object of which they are a part.

If the successive images are spaced slices through one or more organs or tissue, the successive images will not represent true motion and technically there will be no moving image elements from frame to frame. However, since the successive slices through an organ or through tissue will change incrementally, the images are susceptible to being displayed in sequence in the form of a motion picture wherein the depicted objects transform into different shapes and textures through the sequence of images. In the dense motion vector field analysis carried out by the data processor 15 on images representing successive slices, the dense motion vector fields determined by the process will represent displacement between image elements as if the successive frames were frames of a true motion picture. The resulting vectors of the dense motion vector field will represent displacement from frame to frame between corresponding image elements shown in the successive frames.

The dense motion vector fields may be generated in accordance with the system disclosed in the now abandoned Co-pending application Ser. No. 09/593,521, filed Jun. 14, 2000, entitled System for the Estimation of Optical Flow. This application is hereby incorporated by reference.

The dense motion vector fields generated between each pair of adjacent images are generated in both directions between each pair of adjacent images. These dense motion vector fields are then used to generate interpolated images between the images of the original sequence in accordance with the scheme and system described in Co-pending application Ser. No. 09/459,988, U.S. Pat. No. 6,351,545, entitled Motion Picture Enhancing System filed Dec. 14, 1999. This application is hereby incorporated by reference.

As described in application Ser. No. 09/459,988, to generate an interpolated frame between a pair of original images the motion vectors are scaled to correspond to the location of the frame being interpolated in the gap between the original frames. If the interpolated frame is half way between the original images, the magnitudes of both the forward motion vectors and the backward motion vectors are reduced by ½. A first motion adjusted image is then generated from the preceding image of the pair of images and the ½ scale forward vector field. The first motion adjusted image will be derived from the preceding image by moving the image elements of a preceding image in accordance with the ½ scale forward vectors. All of the image elements of the original preceding frame which have a magnitude of zero stay in the same position in the first motion adjusted image. A second motion adjusted image is generated in a similar manner from the succeeding frame of the original pair and ½ scale backward motion vector field. The first and second motion adjusted images are then merged into an interpolated image. In this interpolated image, objects which are displaced from the preceding original frame to the succeeding original frame of the adjacent pair will be located halfway between in the position of such object and the preceding frame and the position of such object and the succeeding frame.

In the accordance with the invention, instead of just interpolating one frame between each adjacent pair of frames in the sequence of original images, several frames may be interpolated equally spaced between each pair of original frames. For example, if two interpolated images are generated between each pair of adjacent frames of the original images, forward and reverse vectors would be scaled at ⅓ and ⅔ to produce two motion adjusted images from the forward vectors and two motion adjusted images from the backward vectors. One motion interpolated image in the interval between the adjacent frames would then be produced from a merger of the motion adjusted image produced from the ⅓ scale forward vectors with the motion adjusted produced from the ⅔ scale backward vectors. The second interpolated image in the interval between the two adjacent frames would be generated by merging the motion adjusted image produced from the ⅔ scale forward vectors with the motion adjusted image produced from the ⅓ scale backward vectors.

After the interpolated images have been generated they are interleaved in the appropriate locations between the original images.

The resulting sequence of images is then stored in the image storage device 17. The images may be displayed in sequence as a motion picture by the video display 19, either by reading out the images from the storage device 17 or displaying them in sequence as they are assembled by the data processor 15.

It is preferable that the images which are displayed as a motion picture be regularly spaced, so that the motion or transformation represented by the display of the images in sequence is not distorted. If the original set of images are not spaced at regular intervals, the interpolation is still used to produce a set of images at regularly spaced intervals between the first image of the original set and the last image of the original set. Most of the intermediate irregularly spaced images of the original set will not have the right spacing. In accordance with one option, these irregularly spaced intermediate images are used only to generate the interpolated images at the proper spacing and are not part of the set of images which are displayed as a motion picture. As an alternative option available to the user, the original images with the wrong spacing are used in the displayed set of images. In this arrangement, each original image will be placed in the closest time slot in the set of images to be displayed. This option may cause some distortion, but it will be hardly noticeable and the option has the advantage of preserving all of the original images, and the information contained therein, in the motion picture display.

In the system as described above, when the medical images are sequences of images in time, the resulting motion picture will show changes in internal organs or tissue with time as smooth motion in the displayed motion picture. When the successive images are successive slices through an organ or through tissue in the body, the resulting displayed motion picture will show how the organs or tissue changes from slice to slice, moving through the body, as a smooth motion picture.

The above description is of a preferred embodiment of the invention and modification may be made thereto without departing from the spirit and scope of the invention, which is defined in the dependant claims.

What is claimed is:

1. A method of displaying medical images comprising generating medical images representing spaced slices through an organ or tissue internally within a body, and displaying said images in sequence as a motion picture, wherein at least one of said images comprises an interpolated image, and wherein said interpolated image is generated from an adjacent pair of images of a first set of said images by generating a dense motion vector field representing displacement between corresponding image elements in adjacent frames of said first set, scaling vectors of said dense motion vector field in accordance with the location of said interpolated image between said adjacent images of said first set to produce a scaled dense motion vector field, and generating an interpolated image in accordance with at least one of said adjacent pair of images of said first set and said scaled dense motion field vector derived from a corresponding adjacent pair of images of said first set.

2. The system of claim 1, comprising at least one of: interleaving said interpolated image between said adjacent pair of said images; displaying said images spaced at regular intervals in said motion picture; and storing said images.

3. A method of displaying medical images comprising generating a first set of related medical images derived from views internally within a body, said first set of images being spaced in time or space, generating a set interpolated images between said first set of images, and assembling a second set of images comprising said interpolated images, and displaying said second set of images as a motion picture, wherein said interpolated images are generated from adjacent pairs of images of said first set by generating dense motion vector fields representing the displacement between corresponding image elements in adjacent frames of said first set, scaling the vectors of said dense motion vector fields in accordance with the location of the interpolated images between the adjacent images of said first set to produce scaled dense motion vector fields, and generating each interpolated image in accordance with at least one of the adjacent pair of images of said first set and the scaled dense motion field vectors derived from the corresponding adjacent pair of images of said first set.

4. A method as recited in claim 3, wherein said related medical images are spaced slices through a organ or tissue.

5. A method as recited in claim 3, wherein said related medical images are spaced in time.

6. The system of claim 3, comprising at least one of: interleaving said interpolated image between said adjacent pair of said images; displaying said images spaced at regular intervals in said motion picture; and storing said images.

7. A system for displaying medical images comprising a medical image generating means for generating a first set of related images from views of spaced slices through an organ or tissue within a human body, and a video display means for displaying said first set of related images as a motion pictures comprising video processing means for generating dense motion vector fields between said images of said first set representing displacement between corresponding image elements in each pair of adjacent images of said first set, for scaling the vectors of said dense motion vector fields in accordance with the location of interpolated images between said images of said first set to provide scaled versions of said dense motion vector fields, and for generating said interpolated images in accordance with said scaled versions of said dense motion vector fields and at least one image of each pair of adjacent images.

8. The system of claim 7, wherein said medical image generating means comprises at least one of:
   an x-ray camera;
   a camera;
   a computer aided tomography (CAT) scan imager;
   a magnetic resonance imaging (MRI) device; and
   a device operative to obtain internal images.

9. The system of claim 7, wherein upon generation of said interpolated images, said interpolated images are interleaved between each of said pairs of adjacent images.

10. The system of claim 7, wherein said images displayed as said motion picture are spaced at regular intervals for display.

11. The system of claim 7, wherein said first set of images and said interpolated images are stored in an image storage means for storing images.

12. A system for displaying medical images comprising a medical image generator adapted to generate a first set of related images from views taken internally within a human body, said images being spaced in time or space, a video processor generates a set of interpolated images from said first set of images and to assemble a second set of images comprising said interpolated images, and a video display device for displaying said second set of images as a motion picture, wherein said video processor generates dense motion vector fields between the images of said first set representing displacement between corresponding image elements in each pair of adjacent images of said first set, said video processor scaling the vectors of said dense motion vector fields in accordance with the location of the interpolated images between the images of said first set to provide scaled versions of said dense motion vector fields, said video processor generating said interpolated images in accordance with the scaled versions of said dense motion vector fields and at least one image of each pair of adjacent images.

13. A system for displaying medical images as recited in claim 12, wherein said first set of medical images are views of spaced slices through an organ or tissue within a body.

14. A system for displaying medical images as recited in claim 12, wherein said first set of medical images are spaced in time.

15. The system of claim 12, wherein said medical image generator comprises at least one of:
   an x-ray camera;
   a camera;
   a computer aided tomography (CAT) scan imager;
   a magnetic resonance imaging (MRI) device; and
   a device operative to obtain internal images.

16. The system of claim 12, wherein upon generation of said interpolated images, said interpolated images are interleaved between each of said pairs of adjacent images.

17. The system of claim 12, wherein said images displayed as said motion picture are spaced at regular intervals for display.

18. The system of claim 12, wherein said first set of images and said interpolated images are stored in an image storage device.

* * * * *